United States Patent
Karim et al.

(10) Patent No.: US 6,620,973 B2
(45) Date of Patent: *Sep. 16, 2003

(54) CATALYSTS FOR OXIDATION OF LOWER OLEFINS TO UNSATURATED ALDEHYDES, METHODS OF MAKING AND USING THE SAME

(75) Inventors: Khalid Karim, Burnage (GB); Yajnavalkya Subrai Bhat, Riyadh (SA); Syed Irshad Zaheer, Riyadh (SA); Asad Ahmad Khan, Riyadh (SA)

(73) Assignee: Saudi Basic Industries Corporation, Riyadh (SA)

(*) Notice: Subject to any disclaimer, the term of this patent is extended or adjusted under 35 U.S.C. 154(b) by 0 days.

This patent is subject to a terminal disclaimer.

(21) Appl. No.: 10/040,039

(22) Filed: Oct. 19, 2001

(65) Prior Publication Data

US 2002/0058847 A1 May 16, 2002

Related U.S. Application Data

(62) Division of application No. 09/560,989, filed on Apr. 28, 2000, now Pat. No. 6,337,424.

(51) Int. Cl.$^7$ .................. C07C 45/27; B01J 23/16; B01J 23/28; B01J 23/31; B01J 23/652
(52) U.S. Cl. .................. 568/478; 568/479; 568/480; 502/306; 502/307; 502/308; 502/309; 502/311; 502/312; 502/313; 502/314; 502/315; 502/316; 502/317; 502/322; 502/248; 502/249; 502/262
(58) Field of Search .................. 502/306–309, 502/311–317, 322, 327, 328, 329, 340, 332, 333–339, 439, 415, 255, 262, 248, 249, 104, 113; 568/478, 470, 476, 479, 480

(56) References Cited

U.S. PATENT DOCUMENTS

| | | | | |
|---|---|---|---|---|
| 4,042,623 A | * | 8/1977 | Ogawa | 260/530 N |
| 4,155,938 A | | 5/1979 | Yamamoto et al. | |
| 4,186,152 A | | 1/1980 | Yamamoto | |
| 4,217,309 A | * | 8/1980 | Umemura et al. | 568/477 |
| 4,224,193 A | | 9/1980 | Vanderspurt | |
| 4,267,385 A | | 5/1981 | Umenura | |
| 4,267,386 A | | 5/1981 | Vanderspurt | |
| 4,380,664 A | | 4/1983 | Ishii et al. | |
| 4,390,736 A | * | 6/1983 | Inoue et al. | 568/801 |
| 4,432,817 A | | 2/1984 | Frankel | |
| 4,438,217 A | | 3/1984 | Takata | |
| 4,442,308 A | | 4/1984 | Arntz | |
| 4,599,430 A | * | 7/1986 | Milberger et al. | 548/548 |
| 4,600,541 A | | 7/1986 | Aoki et al. | |
| 4,916,103 A | | 4/1990 | Martan | |
| 5,072,052 A | | 12/1991 | Boeck | |
| 5,132,269 A | * | 7/1992 | Sasaki et al. | 502/205 |
| 5,144,090 A | | 9/1992 | Honda | |
| 5,153,162 A | * | 10/1992 | Kurimoto et al. | 502/209 |
| 5,206,431 A | * | 4/1993 | Hashiba et al. | 562/534 |
| 5,231,214 A | * | 7/1993 | Ushikubo et al. | 558/319 |
| 5,300,707 A | | 4/1994 | Caillod | |
| 5,380,692 A | * | 1/1995 | Nakatsuji et al. | 502/303 |
| 5,532,199 A | | 7/1996 | Watanabe | |
| 5,618,974 A | * | 4/1997 | Kurimoto et al. | 562/532 |
| 5,907,056 A | * | 5/1999 | Karim et al. | 562/549 |
| 6,013,597 A | * | 1/2000 | Karim et al. | 502/209 |
| 6,028,221 A | * | 2/2000 | Karim et al. | 562/548 |
| 6,080,893 A | | 6/2000 | Hecquet | |
| 6,087,297 A | * | 7/2000 | Karim et al. | 502/303 |
| 6,114,278 A | * | 9/2000 | Karim et al. | 502/312 |
| 6,130,356 A | * | 10/2000 | Karim et al. | 562/548 |
| 6,143,928 A | * | 11/2000 | Karim et al. | 562/534 |
| 6,310,241 B1 | * | 10/2001 | Karim et al. | 562/549 |
| 6,383,977 B1 | * | 5/2002 | Karim et al. | 502/311 |
| 6,441,227 B1 | * | 8/2002 | Karim et al. | 562/548 |

FOREIGN PATENT DOCUMENTS

| | | |
|---|---|---|
| DE | 3300044 | 1/1987 |
| EP | 0 058 046 A | 8/1982 |
| EP | 417723 | 3/1991 |
| EP | 460932 | 12/1991 |
| EP | 861819 | 9/1998 |
| JP | 56055331 | 5/1981 |
| JP | 3170445 | 7/1991 |
| JP | 3294239 | 12/1991 |
| JP | 4295438 | 10/1992 |
| JP | 6031171 | 2/1994 |
| JP | 8003093 | 1/1996 |
| JP | 8040969 | 2/1996 |
| JP | 11343261 | 12/1999 |

OTHER PUBLICATIONS

International Search Report in PCT Appl. No. PCT/EP01/04434 dated Dec. 10, 2001.

* cited by examiner

*Primary Examiner*—Cam N. Nguyen
(74) *Attorney, Agent, or Firm*—Kramer Levin Naftalis & Frankel LLP

(57) ABSTRACT

A catalyst composition for the production of unsaturated aldehydes by the oxidation of the corresponding olefins, and methods of making and using such catalyst compositions. The catalysts of the present invention include compositions of the formula:

$$Mo_a Pd_b Bi_c Fe_d X^1_e X^2_f X^3_g O_z,$$

wherein $X^1$ is an element selected from Co, Ni, V, Pt, Rh, or mixtures thereof; $X^2$ is an element selected from Al, Ga, Ge, Mn, Nb, Zn, Ag, P, Si, W, or mixtures thereof; $X^3$ is an element selected from K, Mg, Rb, Ca, Sr, Ba, Na, In, or mixtures thereof; a is 1; b is $0<b<0.3$; c is $0<c<0.9$; d is $0<d<0.9$; e is $0<e<0.9$; f is $0<f<0.9$; g is $0<g<0.3$; and z is an integer representing the number of oxygen atoms required to satisfy the valency of Mo, Pd, Bi, Fe, $X^1$, $X^2$, and $X^3$ in the catalyst composition. Using the methods of the present invention, one may effectively oxidize the desired starting materials at relatively high levels of conversion, selectivity, and productivity, and with minimal side products.

16 Claims, No Drawings

CATALYSTS FOR OXIDATION OF LOWER OLEFINS TO UNSATURATED ALDEHYDES, METHODS OF MAKING AND USING THE SAME

This is a Divisional of application Ser. No. 09/560,989, filed Apr. 28, 2000, U.S. Pat. No. 6,337,424, issued Jan. 8, 2002.

The redox characteristic of a mixed metal oxide catalyst is a key factor in controlling the activity and oxygenation function of the catalyst. These characteristics depend on the type of metal oxide mixed and their concentration. See, "Oxidative Dehydrogenation of Lower Alkane on Vanadium Based Catalysts", by E. Mamedov and V. Corberan, Applied Catalysis, vol. 217, pages 1–40 (1995). It would be desirable to derive a catalyst composition containing a specific combination of metal elements with suitable properties or characteristics to generate a redox characteristic catalyst having a significant impact on the selectivity and productivity of the oxygenation process. The mixed metal oxide catalysts of the present invention are prepared by an appropriate combination of the metal components, yielding a catalyst with a unique ability to selectively oxidize olefins to alpha-beta unsaturated aldehydes.

SUMMARY OF THE INVENTION

The present invention relates to the selective oxidation of hydrocarbons or olefins in the presence of molecular oxygen to form alpha-beta unsaturated aldehydes. This gas phase reaction is preferably carried out using a mixed metal oxide catalyst at temperatures in the range of 150° C. to 450° C. and at pressures of 1–50 bar. As a result, the method of the present invention achieves relatively high rates of selectivity and productivity.

The catalysts of the present invention are mixed metal oxides of the general formula $$Mo_aPd_bBi_cFe_dX^1_eX^2_fX^3_gO_z,$$

wherein:

X$^1$ is at least one element selected from the group consisting of Co, Ni, V, Pt, and Rh;

X$^2$ is at least one element selected from the group consisting of Al, Ga, Ge, Mn, Nb, Zn, Ag, P, Si, and W;

X$^3$ is at least one element selected from the group consisting of K, Mg, Rb, Ca, Sr, Ba, Na, and In;

a is 1;

b is 0<b<0.3, preferably 0.0000001<b<0.2;

c is 0<c<0.9, preferably 0.0001<c<0.5;

d is 0<d<0.9, preferably 0.0001<d<0.5;

e is 0<e<0.9, preferably 0.0001<e<0.5;

f is 0<f<0.9, preferably 0.0001<f<0.9;

g is 0<g<0.3, preferably 0.0000001<g<0.3; and z is an integer representing the number of oxygen atoms required to satisfy the valency of the remaining components of the formula. The catalysts are preferably produced using the methods disclosed herein.

DETAILED DESCRIPTION OF THE PREFERRED EMBODIMENTS

One aspect of the invention relates to a catalyst for the production of alpha-beta unsaturated aldehydes from olefins and hydrocarbons. According to one embodiment, the catalyst composition has the formula:

$$Mo_aPd_bBi_cFe_dX^1_eX^2_fX^3_gO_z,$$

wherein

X$^1$ is at least one element selected from the group consisting of Co, Ni, V, Pt, and Rh;

X$^2$ is at least one element selected from the group consisting of Al, Ga, Ge, Mn, Nb, Zn, Ag, P, Si, and W;

X$^3$ is at least one element selected from the group consisting of K, Mg, Rb, Ca, Sr, Ba, Na, and In;

a is 1;

b is 0≦b<0.3, preferably 0.0000001<b<0.2;

c is 0≦c<0.9, preferably 0.0001<c<0.5;

d is 0≦d<0.9, preferably 0.0001<d<0.5;

e is 0≦e<0.9, preferably 0.0001<e<0.5;

f is 0≦f<0.9, preferably 0.0001<f<0.9;

g is 0≦g<0.3, preferably 0.0000001<g<0.3; and z is an integer representing the number of oxygen atoms required to satisfy the valency of the remaining components of the formula.

According to a preferred embodiment of the invention, the catalyst composition has the general formula $$Mo_aPd_bBi_cFe_dX^1_eX^2_fX^3_gO_z,$$

wherein:

X$^1$ is at least one element selected from the group consisting of Co, Ni, V, Pt, and Rh;

X$^2$ is at least one element selected from the group consisting of Al, Ga, Ge, Mn, Nb, Zn, Ag, P, Si, and W;

X$^3$ is at least one element selected from the group consisting of K, Mg, Rb, Ca, Sr, Ba, Na, and In;

a is 1;

b is 0<b<0.3, preferably 0.0000001<b<0.2;

c is 0<c<0.9, preferably 0.0001<c<0.5;

d is 0<d<0.9, preferably 0.0001<d<0.5;

e is 0<e<0.9, preferably 0.0001<e<0.5;

f is 0<f<0.9, preferably 0.0001<f<0.9;

g is 0<g<0.3, preferably 0.0000001<g<0.3; and z is an integer representing the number of oxygen atoms required to satisfy the valency of the remaining components of the formula. The catalysts are preferably produced using the methods disclosed herein.

Preferably, the catalyst is prepared from a solution of soluble compounds (salts, complexes, or other compounds) of each of the metals. The solution is preferably an aqueous system having a pH of 1 to 10, and more preferably at a pH of 1 to 7, and the solution is maintained at a temperature of about 30° C. to about 100° C. Water is removed by filtration to complete dryness, at which point the catalyst is dried in an oven at 100° C. to 130° C. for about 4 to about 24 hours. The dried catalyst is calcined by heating to about 250° C. to about 600° C., about 250° C. to about 450° C., in air or oxygen for about one hour to about 16 hours to produce the desired catalyst composition.

The catalyst may be used with or without a support. If desired, suitable supports include alumina, silica, titania, zirconia, zeolites, silicon carbide, molybdenum carbide, molecular sieves, microporous materials, nonporous materials and mixtures thereof. Support material can be pretreated with acids such as HCl, $HNO_3$, $H_2SO_4$, per acids or heteroploy acids of phosphorous tungstate or silicotunstate, and alkali bases such as KOH or NaOH. When used on a support, the support usually comprises from about 50 to 95% by weight of the catalyst composition, with the remainder being the catalyst composition.

Preferably, molybdenum is introduced into the solution as an ammonium salt, such as ammonium paramolybdate, or as an organic acid salt of molybdenum. such as acetates, oxalates, mandelates, and glycolates. Some other partially water soluble molybdenum compounds which may be used in the present invention include molybdenum oxides, molybdic acid, and molybdenum chlorides.

Preferably, vanadium, bismuth, iron, cobalt, aluminum, gallium, silicon, germanium, antimony, phosphorous, niobium, potassium, magnesium palladium, tungsten, manganese are introduced as salts or acids, oxides, hydrate oxides, acetates, chlorides, nitrates, oxalates, or tartrates.

The method of the present invention is suitable for oxidation of hydrocarbons and olefins to alpha-beta unsaturated aldehydes. Preferably, the feedstock includes lower branched or straight-chained alkanes or alkenes, having $C_2$–$C_6$ carbon atoms. Further, the inventive catalyst can also be applied for the ammoxidation of $C_2$–$C_5$. In a preferred embodiment the starting material is propylene and acrolein is produced by the method.

The reaction mixture used in the method of the present invention is generally a gaseous mixture of 0.1 to 99 mol % olefins, such as propylene, 0.1 to 99 mol % molecular oxygen, either as pure oxygen or in the form of air, 0 to 50 mol % water, in the form of steam, and 0 to 90 mol % nitrogen or another inert gas. The gaseous mixture is generally introduced into the reaction zone at a temperature of about 150° C. to about 500° C., preferably from 250° C. to 450° C. The reaction zone generally has a pressure of from 1 to 50 bar, and preferably 1 to 30 bar. The contact time between the reaction mixture and the catalyst is preferably about 0.01 second to 100 seconds, and more preferably 0.1 second to 10 seconds, and the space hourly velocity is about 50 to about 50,000 $h^{-1}$, preferably about 100 to about 20,000 $h^{-1}$, and more preferably from 500 to 10,000 $h^{-1}$.

According to one preferred embodiment, the method comprises contacting a feed mixture comprising 1–50% by volume of olefins, 0.25 to 50% by volume oxygen or a gas capable of providing oxygen, 0–50% by volume steam and 10–80% by volume inert gas at a temperature of 170 to 450° C. at a pressure of 15–500 psi at a space velocity of 500–20,000 hr–1 with the catalyst. Preferably, the method provides a conversion greater than 90%, more preferably greater than 95%, most preferably greater than 98%, and a selectivity greater than 85%, more preferably greater than 90%, most preferably greater than 95%. of the olefins to the unsaturated aldehydes.

The process is generally carried out in a single stage in a fixed bed or fluidized bed or solid moving bed reactor with all the oxygen and reactants being supplied as a single feed and unreacted starting materials being recycled. However, multiple stage addition of oxygen to the reactor with intermediate hydrocarbon feed can be used. This may improve productivity and avoid a potentially hazardous condition.

The following examples are intended to be illustrative of this invention. They are, of course, not to be taken to in any way limit the scope of this invention. Numerous changes and modifications can be made with respect to the invention without departing from the spirit or scope of the present invention.

EXAMPLES

Example 1

$Mo_1Pd_{01.57e-4}Bi_{0.09}Co_{0.8}Fe_{0.2}Al_{0.123}V_{4.69e-3}K_{5.33e-3}$

Ammonium metavanadate (Aldrich Chemicals, Assay= 99.0%), 0.11 grams, was added to distilled water and heated to 90° C. with stirring. A yellow colored solution with pH between 4 and 7 was obtained (solution A). Bismuth nitrate, 8.75 g, 16.2 grams of ferric nitrate, and 46.68 grams of cobaltus nitrate were added with water to solution A with continuous stirring. Thereafter, the required amount of palladium, potassium and aluminum salt solutions were slowly added to the mixture. Ammonium paramolybdate tetrahydrate (Aldrich Chemicals A.C.S -12054-85-2), 35.4 grams, was added to the solution. This mixture was then dried. The resulting solid was dried in an oven at 100–120° C. The dried material was cooled to room temperature and calcined in the range of 300 to 600° C. Calcined catalyst was formulated into uniform particles of 40–60 mesh size and loaded in a stainless steel fixed bed tubular autoclave reactor.

The catalyst was tested with a gas feed composition of nitrogen:oxygen:propylene:water in the ratio of 77:7.50:5.50:10 at 342° C., at a pressure of 15 psi, and a total flow of 130 cc/min. The reaction product showed a 99% conversion of propylene with a 98% selectivity for acrolein.

Example 2

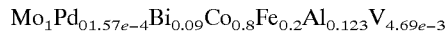

$Mo_1Pd_{01.57e-4}Bi_{0.09}Co_{0.8}Fe_{0.2}Al_{0.123}V_{4.69e-3}$

Ammonium metavanadate (Aldrich Chemicals, Assay= 99.0%), 0.11 grams, was added to distilled water and heated to 90° C. with stirring. A yellow colored solution with pH between 4 and 7 was obtained (Solution A). Bismuth nitrate, 8.75 g, 16.2 grams of ferric nitrate, and 46.68 grams of cobaltus nitrate were added with water to solution A with continuous stirring, followed by the addition of the required amount of palladium and aluminum salts solution slowly to the mixture. Thereafter, ammonium 35.4 g paramolybdate tetrahydrate (Aldrich Chemicals A.C.S -12054-85-2) was added to the above solution. This mixture was then dried and the resulting solid was dried in an oven at 100–120° C. The dried material was cooled to room temperature and calcined in the range of 300 to 600° C. Calcined catalyst was formulated into uniform particles of 40–60 mesh size and loaded in a stainless steel fixed bed tubular autoclave reactor.

The catalyst was tested with a gas feed composition of nitrogen:oxygen:propylene:water in the ratio of 77:7.50:5.50:10 at 342° C., at a pressure of 15 psi and a total flow of 130 cc/min. The reaction product showed a 93.2% conversion of propylene with a 87.4% selectivity for acrolein

Example 3

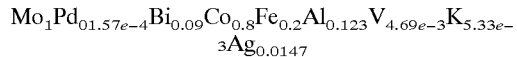

$Mo_1Pd_{01.57e-4}Bi_{0.09}Co_{0.8}Fe_{0.2}Al_{0.123}V_{4.69e-3}K_{5.33e-3}Ag_{0.0147}$

Ammonium metavanadate (Aldrich Chemicals, Assay= 99.0%), 0.11 grams, was added to distilled water and heated to 90° C. with stirring. A yellow colored solution with pH between 4 and 7 was obtained (Solution A). Bismuth nitrate, 8.75 g, 16.2 grams of ferric nitrate, and 46.68 grams of cobaltus nitrate were added with water to solution A with continuous stirring, at which point the required amount of palladium, potassium, silver, and aluminum salt solutions were slowly to the mixture. Thereafter, 35.4 g ammonium paramolybdate tetrahydrate (Aldrich Chemicals A.C.S -12054-85-2) was added to the solution. This mixture was then dried and the resulting solid was dried in an oven at 100–120° C. The dried material was cooled to room temperature and calcined in range of 300 to 600° C. Calcined catalyst was formulated into uniform particles of 40–60 mesh size and loaded in a stainless steel fixed bed tubular autoclave reactor.

The catalyst was tested with a gas feed composition of nitrogen:oxygen:propylene:water in the ratio of 77:7.50:5.50:10 at 342° C., at a pressure of 15 psi, and a total flow of 130 cc/min. The reaction product showed a 97% conversion of propylene with a 98.6% selectivity for acrolein.

The catalysts disclosed in the present application exhibit modified optimum redox behavior resulting in higher activity and yields towards the oxygenated products. Further, the inventive catalyst showed no deactivation until 8000 hrs on stream and achieved similar or higher yields (>95%) at relatively lower temperatures than mentioned in the prior art.

The above description of the invention is intended to be illustrative and not limiting. Various changes or modifications in the embodiments described may occur to those skilled in the art. These can be made without departing from the spirit or scope of the invention.

What is claimed is:

1. A method for performing a catalytic chemical reaction in fluid phase for converting one or more fluid phase reactants to one or more fluid phase products comprising contacting a mixture containing said one or more fluid phase reactants with a catalyst under suitable reaction conditions in a reaction zone to form said one or more fluid phase products, said catalyst containing a catalyst composition of the formula:

$$Mo_a Pd_b Bi_c Fe_d X^1_e X^2_f X^3_g O_z,$$

wherein:
   $X^1$ is at least one element selected from the group consisting of Co, Ni, V, Pt, and Rh;
   $X^2$ is at least one element selected from the group consisting of Al, Ga, Ge, Mn, Nb, Zn, Ag, P, Si, and W;
   $X^3$ is at least one element selected from the group consisting of K, Mg, Rb, Ca, Sr, Ba, Na, and In;
   a is 1;
   b is $0<b<0.3$;
   c is $0<c<0.9$;
   d is $0<d<0.9$;
   e is $0<e<0.9$;
   f is $0<f<0.9$;
   g is $0<g<0.3$; and
   z is an integer representing the number of oxygen atoms required to satisfy the valency of Mo, Pd, Bi, Fe, $X^1$, $X^2$, and $X^3$ in the catalyst composition.

2. The method of claim 1, wherein said one or more fluid phase reactants comprise molecular oxygen.

3. The method of claim 1, wherein said one or more fluid phase reactants comprise olefin and said one or more fluid phase products comprise corresponding unsaturated aldehydes.

4. The method of claim 1, wherein said one or more fluid phase reactants comprise propylene and said one or more fluid phase products comprise acrolein.

5. The method of claim 1, wherein said one or more fluid phase reactants comprise $C_2$–$C_5$ olefins and oxygen and said one or more fluid phase products comprise corresponding alpha-beta unsaturated aldehydes.

6. The method of claim 1, wherein said method is performed using a feed mixture comprising butylene and said method produces corresponding methacrolein.

7. The method of claim 1, wherein said method is performed using a feed mixture comprising $C_2$–$C_5$ alkanes, $C_2$–$C_5$ alkenes or mixtures thereof and said method produces corresponding alpha-beta unsaturated aldehydes.

8. A catalyst for the production of unsaturated aldehydes from olefins, said catalyst comprising a catalyst composition having the formula:

$$Mo_a Pd_b Bi_c Fe_d X^1_e X^2_f X^3_g O_z,$$

wherein:
   $X^1$ is at least one element selected from the group consisting of Co, Ni, V, Pt, and Rh;
   $X^2$ is at least one element selected from the group consisting of Al, Ga, Ge, Mn, Nb, Zn, Ag, P, Si, and W;
   $X^3$ is at least one element selected from the group consisting of K, Mg, Rb, Ca, Sr, Ba, Na, and In;
   a is 1;
   b is $0<b<0.3$;
   c is $0<c<0.9$;
   d is $0<d<0.9$;
   e is $0<e<0.9$;
   f is $0<f<0.9$;
   g is $0<g<0.3$; and
   z is an integer representing the number of oxygen atoms required to satisfy the valency of Mo, Pd, Bi, Fe, $X^1$, $X^2$, and $X^3$ in the catalyst composition.

9. The catalyst of claim 8, further comprising a support.

10. The catalyst of claim 9, wherein said support is selected from the group consisting of alumina, silica, titania, zirconia, zeolites, silicon carbide, Mo-carbide, molecular sieves, microporous materials, nonporous materials, and mixtures thereof.

11. The catalyst of claim 9, wherein the support is pretreated with an acid or base.

12. The catalyst of claim the 9, wherein the supported catalyst comprises from about 5–50% by weight of the catalyst composition, with remainder being the support material.

13. A process for making the catalyst of claim 8, comprising:
   (a) forming a mixture Mo, Pd, Bi, Fe, $X^1$, $X^2$, and $X^3$ in a solution;
   (b) drying said mixture to form a dried solid material; and
   (c) calcining said dried solid material to form said catalyst.

14. The process of claim 13, wherein said mixture is an aqueous system having a pH from 1 to 10.

15. The process of claim 13, wherein said mixture is an aqueous system having a pH from 1 to 7.

16. The process of claim 13, wherein said calcining comprises heating said dried solid material at a calcining temperature from about 250 to 450° C. in air or oxygen for a period of time from about one hour to about 16 hours.

* * * * *